(12) United States Patent
Cao et al.

(10) Patent No.: US 8,998,616 B2
(45) Date of Patent: Apr. 7, 2015

(54) LASER CURETTAGE

(75) Inventors: Densen Cao, Sandy, UT (US); Steven Jensen, West Jordan, UT (US)

(73) Assignee: CAO Group, Inc., West Jordan, UT (US)

( * ) Notice: Subject to any disclaimer, the term of this patent is extended or adjusted under 35 U.S.C. 154(b) by 1561 days.

(21) Appl. No.: 11/998,039

(22) Filed: Nov. 28, 2007

(65) Prior Publication Data

US 2009/0092947 A1 Apr. 9, 2009

Related U.S. Application Data

(63) Continuation-in-part of application No. 11/382,586, filed on May 10, 2006, now abandoned.

(60) Provisional application No. 60/689,365, filed on Jun. 10, 2005.

(51) Int. Cl.
| | | |
|---|---|---|
| *A61C 17/00* | (2006.01) | |
| *A61C 17/028* | (2006.01) | |
| *A61C 1/18* | (2006.01) | |
| *A61C 1/00* | (2006.01) | |
| *A61K 31/155* | (2006.01) | |
| *A61K 33/00* | (2006.01) | |
| *A61K 33/40* | (2006.01) | |
| *A61K 41/00* | (2006.01) | |
| *A61K 45/06* | (2006.01) | |

(52) U.S. Cl.
CPC ............. *A61C 1/0046* (2013.01); *A61K 31/155* (2013.01); *A61K 33/00* (2013.01); *A61K 33/40* (2013.01); *A61K 41/00* (2013.01); *A61K 45/06* (2013.01); *Y10S 514/90* (2013.01)

(58) Field of Classification Search
USPC .............................. 433/29, 215; 514/900, 902
See application file for complete search history.

(56) References Cited

U.S. PATENT DOCUMENTS

| 6,039,565 A * | 3/2000 | Chou et al. ...................... 433/29 |
| 2003/0059379 A1 * | 3/2003 | Andersen et al. ............... 424/49 |
| 2005/0271602 A1 * | 12/2005 | Milanovich et al. ............ 424/49 |

FOREIGN PATENT DOCUMENTS

WO  WO 99/39652  * 8/1999

* cited by examiner

*Primary Examiner* — Lezah Roberts
(74) *Attorney, Agent, or Firm* — CAO Group, Inc.; Terry S. Jones

(57) ABSTRACT

Laser ablation is used in curettage to treat periodontal disease. After an initial step of ablating afflicted tissues, an anti-microbial rinse is applied. A flexible fiber optic guide is the preferred means of directing radiant energy to the afflicted tissues. Sulcular disinfection may also be achieved by similar associated processes. Various anti-microbial agents and laser sources are disclosed.

12 Claims, 7 Drawing Sheets

LASER CURETTAGE

CROSS REFERENCE TO RELATED APPLICATIONS

This application is a continuation-in-part of U.S. application Ser. No. 11/382,586, entitled "Method for Treating Periodontal Disease," filed May 10, 2006, now abandoned which claims the benefit of U.S. Provisional Application No. 60/689,365, filed Jun. 10, 2005.

FIELD OF THE INVENTION

The present invention relates to the field of treatment of periodontal disease and, more particularly, relates to treating periodontal disease with a laser and chemical combination.

BACKGROUND OF INVENTION

Periodontal disease is a pathogenic infection of the gums which is common among all humans and animals. The disease provides a major pathway to the loss of teeth and oral bone throughout every society, leading to extreme personal discomfort among the afflicted. Given the prevalence of the disease and related costs, effective treatments of the disease and prevention strategies are continually being pursued.

A major contributor to periodontal disease concerns the oral environment. The oral environment provides a warm moist cavity that is full of nutrients, making it an excellent location to incubate microbes. It is not surprising, therefore, that pathogens readily ingress into periodontal pockets where the infection occurs. In the milder forms of periodontal disease—commonly referred to as gingivitis—the gums redden, swell and bleed easily. Gingivitis is limited to the soft tissue surrounding the tooth and does not typically result in bone loss. This stage of the disease is reversible with treatment and proper oral care. On the other hand, uncontrolled or rampant periodontal infection leads to advanced stages of the disease called periodontitis. Left untreated, periodontitis causes progressive bone loss around teeth that ultimately results in the teeth becoming loose from their sockets. There are few if any characteristic stages of progression, as the driving actions underlying the disease are the same—e.g., accumulation of bacteria at the gum line leading to the formation of dental plaque. A specific treatment of the disease depends primarily on the extent of the disease—e.g., the extent of the infection or the formation of plaque.

Some common characteristics of the disease are as follows. First, there occurs an accumulation of bacteria at the gum line that forms bacterial or dental plaque. Bacterial plaque later calcifies to form calculus, which can exist both above and below the gum line. At the same time, there occurs a sustained dramatic change in the normal micro flora existing below the gum line in the region between the gum and tooth—typically referred to as the gingival margin. Disease causing microbes find a safe home in the gingival margin, where they are safe from the tongue and major saliva pathways, thereby upsetting the balance of micro flora. The rogue microbes begin to emit enzymes that destroy the connective tissue between teeth and gums which creates a "periodontal pocket." Because the mouth acts as an incubator with a good supply of nutrition, microbes flourish in the periodontal pockets. Dentists use a tool called a periodontal probe to measure pocket depths of individual patients. This provides a measure of the depth the rogue microbes have eaten the connective tissue away. The deeper the periodontal pocket goes, the more difficult it is to treat. When the pockets are near the surface (say about less than 3 mm) the pocket can in some cases be treated with a sulcular disinfection regime as disclosed in commonly owned U.S. patent application Ser. No. 11/382,586. An appropriate disinfection regime can bring back into balance the normal micro flora and allow healing to occur.

There are two different issues a clinician must address in order to cure periodontal disease. The first obviously is the restoration of the normal micro flora, while the second is to restore the pocket to its normal state, at least to the extent possible. If the periodontal pocket is greater than 3 mm, then sulcular disinfection will not work because it only addresses one part of the problem—the microbes. This presents a major problem with periodontal pockets—even though you disinfect them, rogue microbes can easily migrate back into the deep protective pockets and start where they left off. One can continuously treat deep pockets and slow down the disease with a disinfection regime, but one will rarely restore the pockets to their pre-infection condition. Deep pockets provide too big a space for microbes and therefore require a different procedure in order to have some chance of success.

The laser curettage treatment described herein provides certain advantages that will advance the treatment and prognosis for patients suffering advanced stages of the disease—i.e., to the point where deep pockets have developed. Curettage is a procedure used by many periodontists, and consists of using small hand instruments to physically scrape away the diseased lining of epithelial cells from the bottom of the pocket. The idea is to scrape away the diseased tissue and, at the same time, cause a slight wound. The wound is key to decreasing pocket depth. And if there are insufficient interfering microbes the new gingival tissue will grow back higher on the tooth. Through multiple curettage treatments it is possible to eliminate the pocket entirely.

The curettage procedure described above has been used successfully on many patients. As described and disclosed below, the present invention dispenses with the use of hand instruments to destroy the diseased epithelial lining and, instead, uses a laser and a powerful disinfection regime. Specifically, while standard curettage comprises a physical scraping of tissue, the present invention achieves that result through the process of laser ablation of tissue combined with flooding the pocket with an anti-microbial solution. While lasers have been used in the treatment of periodontal disease, such treatments appear generally limited to photodynamic therapies, as disclosed, for example, in U.S. Patent Application Publication 2004/0259053 (Bekov et al.).

Recently, lasers have been used to treat periodontal disease by using a fiber-optic guide to direct laser energy into periodontal pockets to kill bacteria. One approach using this technique is disclosed, for example, in U.S. Pat. No. 6,663,386 (Moelsgaard). This less invasive and painful form of treatment does have its limitations, however, in that the laser is limited by the relative size of the guide and the ability to adequately control its direction. As such, areas needing treatment may not be adequately treated or can be missed entirely. What is needed is a method to improve upon the use of the laser treatment of periodontal disease for maximum coverage and disinfection of the treated area.

BRIEF SUMMARY OF THE INVENTION

In view of the foregoing disadvantages inherent in the known types of treatment of periodontal disease, this invention provides a new and improved method of treatment merging the benefits of laser ablation and chemical treatment. As such, the present invention's general purpose is to provide a new and improved method that is both safe and efficient, providing a broader treatment area than that obtained through use of a laser guide alone or in conjunction with a cooling spray of water or water and air with minimal resulting discomfort to the patient.

The present invention provides an improved method for treating periodontal disease. The method comprises the use of a laser or radiant energy source that is tuned to ablate the cells and tissue comprising the gingival margin in the periodontal pocket below and in the region of the gum line. The laser light is applied to infected periodontal pockets with the intention of destroying through ablation the infected cells and tissue that make up the diseased epithelial lining, together with any susceptible pathogens. The periodontal pocket is then flushed with an anti-microbial substance with the intention to destroy any residual susceptible pathogens. The advantage of the flushing is that any residual organisms have been already weakened by the applied laser light and the use of a liquid anti-microbial substance will reach areas missed by the direction of the guide.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

Figure 1:
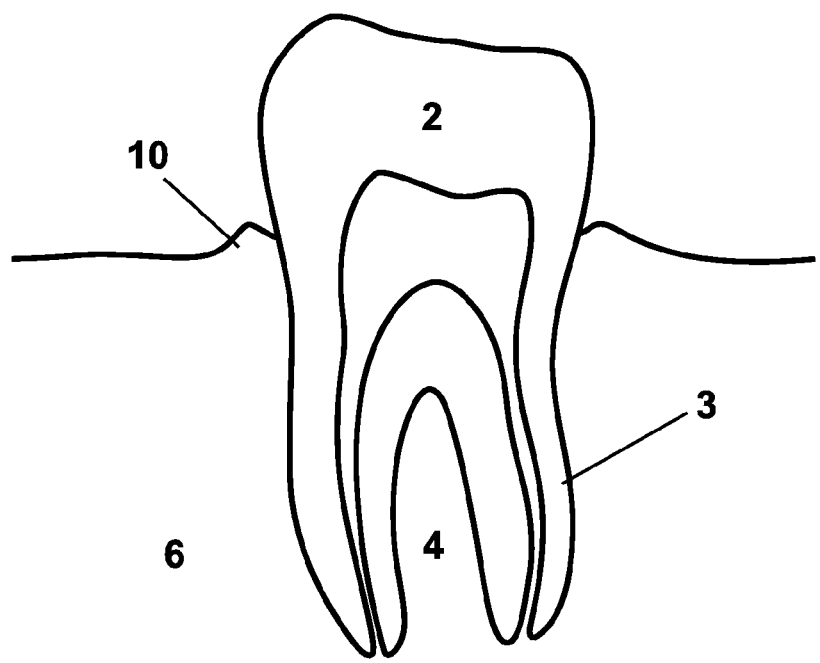
FIG. 1 is a partial sectional view of a normal tooth and surrounding tissue.
Figure 2:
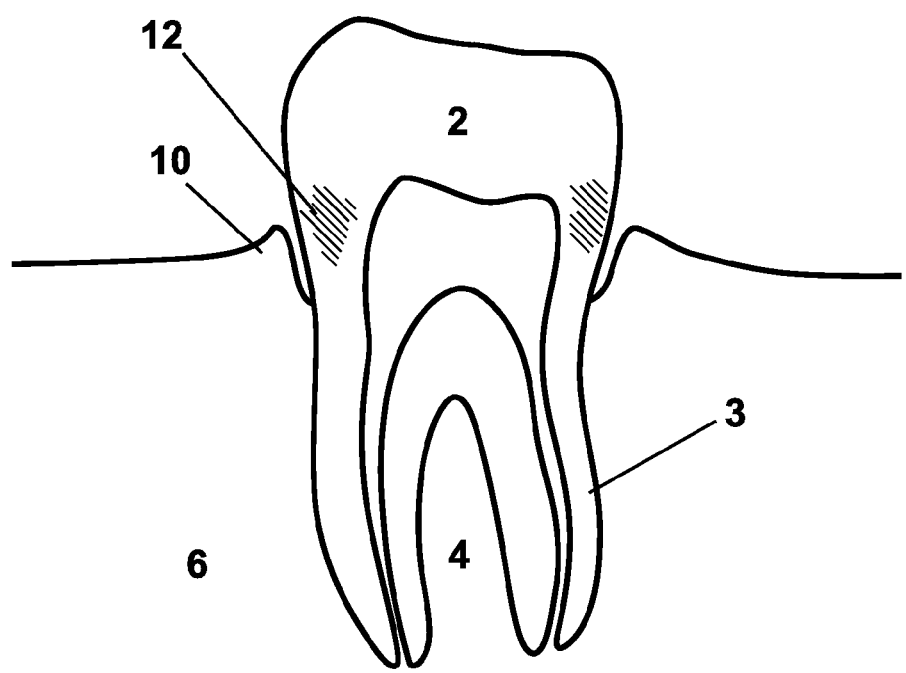
FIG. 2 is the tooth and surrounding tissue of FIG. 1 having developed an early stage of gingivitis.
Figure 3:
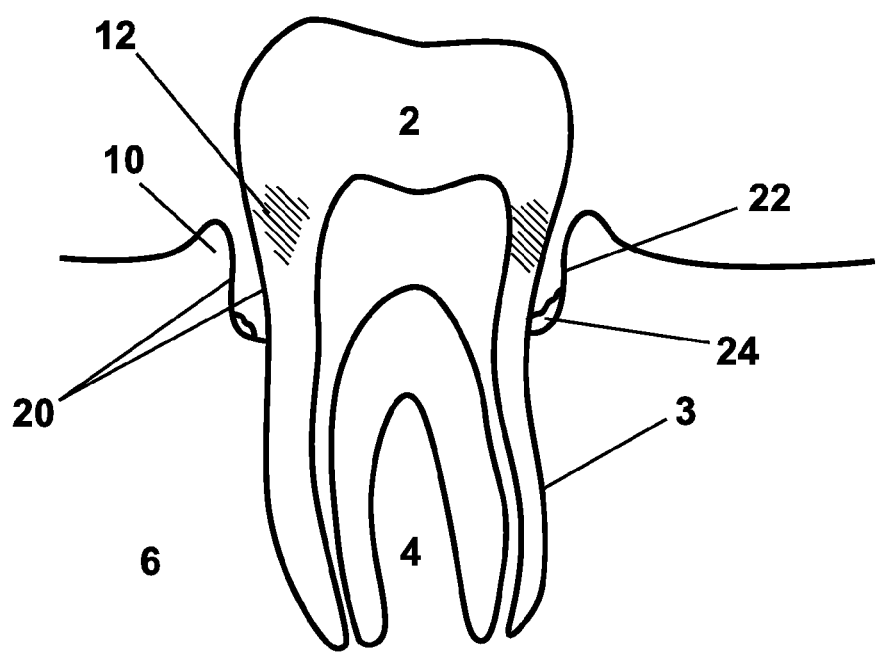
FIG. 3 is the tooth and surrounding tissue of FIG. 2 having developed advanced periodontal disease.

With reference now to the drawings, the preferred embodiment of the method of periodontal treatment is herein described. It should be noted that the articles "a", "an" and "the", as used in this specification, include plural referents unless the content clearly dictates otherwise. With reference to FIG. 1, a healthy tooth 2 rests in a bony socket 4 in the jaw 6. The entire area is covered by the gingiva 10, or "gums." Over time, if left without proper oral care, tartar 12 will build up against tooth 2 (shown in FIG. 2), causing the gums 10 to recede away from the tooth and exposing the root 3 of the tooth 2 in a condition called "gingivitis." FIG. 3 illustrates a condition further deteriorated from gingivitis, or the so-called peridontitis. Where periodontitis has occurred, the gums 10 have receded to the point of forming an open pocket 20 around the tooth 2 and its root system 3. The pocket 20 is filled with inflamed tissue 22 and infectious matter 24. If left untreated the tooth 2 and socket 4 may deteriorate, causing loss of the tooth 2.

Figure 4:
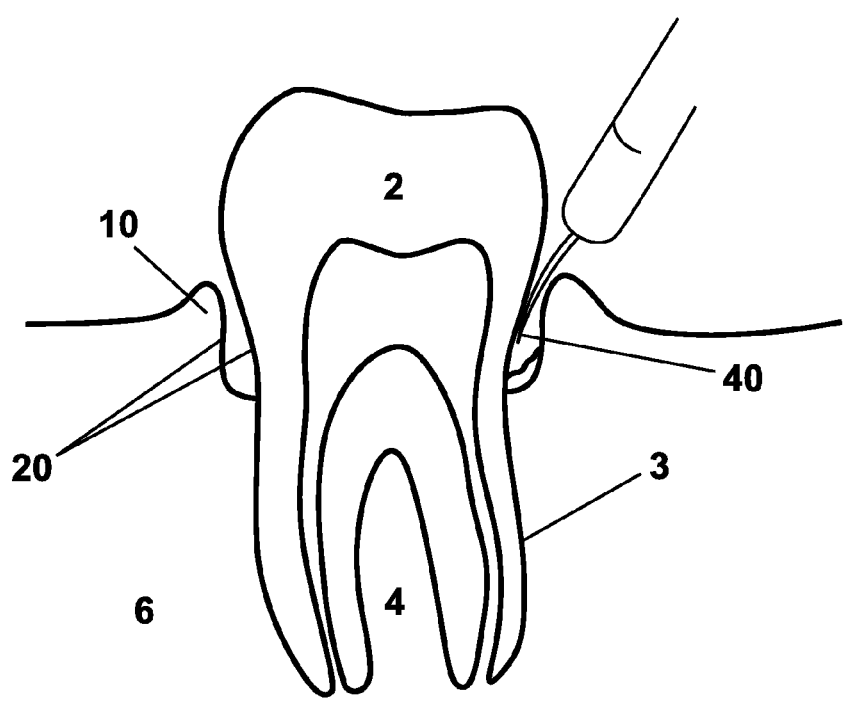
FIG. 4 is the tooth and surrounding tissue of FIG. 3, being treated by a fiber optic guide through which laser light is being transmitted.
Figure 5:
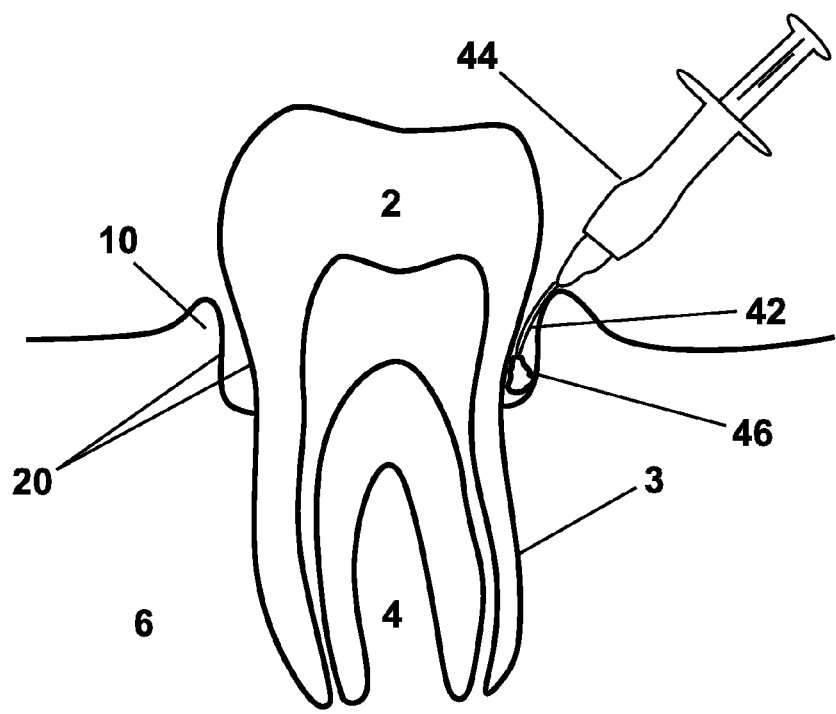
FIG. 5 is tooth and surrounding tissue of FIG. 4 being flushed with an anti-microbial substance by the means of a slender tip attached to a syringe.

Treatment of the condition is shown in FIGS. 4 and 5. The method harnesses the benefits of a radiant energy source that is of sufficient strength to ablate the cells and tissue that comprise the lining of the open pocket 20 and the inflamed tissue 22. The process of ablation is coupled with flooding the pocket region with anti-microbial agents that are chemically lethal to a wide variety of pathogens. The combined effect of ablation by radiant energy and flooding with anti-microbial agents is intended to provide a "wound" to the epithelial lining through ablation of cells and tissue and, at the same time, to destroy a broad spectrum of pathogens, such that remaining pathogens can eventually be controlled by the normal functions of the immune system. The healing process of the wound creates a healthy tissue that reduces pocket size, thereby restoring the gum region to its pre-periodontitis state.

The method warrants a radiant energy source with sufficient energy to become not only lethal to pathogens, but to destroy through ablation the cells and tissue that comprise the epithelial lining or the lining of the open pocket 20 and the inflamed tissue 22. The radiant energy can be produced from sources such as a diode laser, examples of which are the gallium nitride, aluminum gallium arsenide diode laser and the like. The radiant energy can be produced from sources such as high intensity light from incandescent, halogen or plasma arc devices. The radiant energy can be produced from sources such as solid state lasers, examples of which are neodymium YAG, titanium sapphire, thulium YAG, ytterbium YAG, Ruby, holmium YAG lasers and the like. The radiant energy can be produced from sources such as EB or electron beam devices. The radiant energy can be produced from sources such as gas lasers, examples of which include carbon dioxide gas, argon gas, xenon gas, nitrogen gas, helium-neon gas, carbon monoxide gas, and hydrogen fluoride gas lasers and the like. There are also many dye lasers that utilize a radiant energy source that pass through or are absorbed by various dyes or stains to achieve various incident energies or flux densities at specific wavelengths. Dye lasers are also within the scope of this method.

The method also warrants an anti-microbial substance that is capable of destroying pathogens. There are numerous substances with anti-microbial or anti-pathogenic activity. Any substance that is capable of destroying or stemming the growth of a pathogen is within the scope of this method. A few possible examples of antimicrobial substances include: ethanol, isopropanol, methyl paraben, ethyl paraben, butyl paraben, propyl paraben, hydrogen peroxide, carbamide peroxide, eugenol, sodium chlorite, chlorhexidine, chlorhexidine gluconate, sodium chlorite, thymol, cetyl pyridinium chloride, chloroxylenol, iodine, hexachlorophene, triclosan, quaternary ammonium compounds, sodium hypochlorite, calcium hypochlorite, or any like substance that is capable of destroying or limiting the reproduction of pathogens.

Many of these antimicrobial agents are a dry powder in their raw form and would benefit by being dissolved into a solvent. Liquid antimicrobial agents are able to migrate easier into difficult areas, thus having an advantage over powders. A few examples of possible solvents include: water, propylene glycol, glycerin, polysorbates, liquid polyethylene glycols, ethanol or any solvent capable of dissolving or liquefying an antimicrobial substance.

Optionally, the antimicrobial agent can contain additional components that would improve patient comfort such as a flavor, sweetener or anesthetic. A few possible substances that would aid in patient comfort include: sodium saccharin, phenylalanine, benzocaine, lidocaine, dyclonine hydrochloride, peppermint oil, spearmint oil, methyl salicylate and any like substance.

Numerous formulas are capable of being produced during the practice of this method. Compositions may be made in any combination according to the following Table A, dependant upon the desired agents used and overall effect.

TABLE A

| Rinse Component | Percentage by Total Weight | Function |
| --- | --- | --- |
| Antimicrobial agent | 0.01%-100% | Kill bacteria |
| Solvent | 0%-99.99% | Allows the rinse to be a fluid that will easily flow into a periodontal pocket. |
| Flavoring | 0%-5% | Make the rinse palatable. |
| Anesthetic | 0%-30% | Reduce patient discomfort. |

A few specific examples include:
Formula #1
  6.0%—chlorhexidine gluconate 20% aqueous
  94.0%—Water
Formula #2
  1%—chlorhexidine
  99.0%—Water
Formula #3
  5.0%—sodium hypochlorite
  95.0%—Water
Formula #4
  1.0%—calcium chlorite
  99.0%—Water
Formula #5
  0.5%—sodium chlorite
  99.5.0%—Water
Formula #6
  10.0%—chlorhexidine gluconate 20% aqueous
  73.4%—Water
  0.3%—peppermint oil
  15.0%—ethanol
  0.3%—Phenylalanine
  1.0%—dyclonine hydrochloride
Formula #7
  3.0%—hydrogen peroxide
  55.4%—glycerin
  0.3%—peppermint oil
  40.0%—water
  0.3%—Phenylalanine
  1.0%—benzocaine
Formula #8
  1.0%—methyl paraben
  25.0%—Water
  0.3%—methyl salicylate
  25.0%—ethanol
  0.3%—sodium saccharin
  1.0%—lidocaine
  47.4%—propylene glycol The above example formulas are sufficiently adequate over one or multiple applications to destroy or limit the growth of pathogens in the oral environment.

A typical procedure of events during a routine periodontal treatment regime would be to first identify areas of greatest infection. These areas would be selected for greatest exposure to radiant energy. Referring to FIG. 4, the radiant energy source would be focused into these infected pockets by means of a thin fiber optic guide 40, the fiber optic guide being small enough to be directed between the teeth and gums. The periodontal pocket 20 is then radiated with radiant energy while the optical fiber 40 is moved in increments around the gums 10. As illustrated in FIG. 5, once the treatment of the gums by radiant energy is complete, the periodontal pocket 20 is flushed with an antimicrobial fluid 46 by means of a small tip 42 attached to a syringe 44. The treatment regime may include multiple treatments, the number of which depends on the degree of infection present. The treatment regime usually continues until the pocket 20 has filled in substantially from its state of periodontitis. Following the filling in of the pocket 20, a regime of sulcular disinfection may be continued until swelling and redness of infected gums is no longer apparent and only pink healthy gums persist.

The treatment regime can also begin by flushing the periodontal pockets with antimicrobial agents, followed by radiating with radiant energy. This would allow any additional anisthetic contained in the antimicrobial agent to anesthetize the working area prior to receiving radiant energy, and may prove particularly helpful and beneficial where substantial or repetitive ablation occurs during the process of laser curettage.

In yet a further embodiment of the present invention, a 1% chlorhexidine gluconate irrigation solution is used in conjunction with an 810 nm diode laser. The solution may contain a mild anesthetic and, if desired, be flavored. The solution is delivered using a syringe having a capacity of about 1 cc, although larger or smaller syringes may be used. The above described irrigation solution is designed for irrigation into the periodontal pockets prior to their being irradiated with the 810 nm laser light. The synergistic application of this broad-spectrum anti-microbial solution in conjunction with 810 nm laser light provides an excellent treatment in the control of early-stage periodontal disease—e.g., the gingivitis stage. Indeed, independent research by the inventors indicates that when treatment of early-stage periodontal disease using the combined irrigation solution and 810 nm laser is performed, the combination provides an increase in the kill rate of an isolated strain of bacterium—e.g., *streptococcus mutans*—by 11% over chlorhexidine solution alone.

Figure 6:
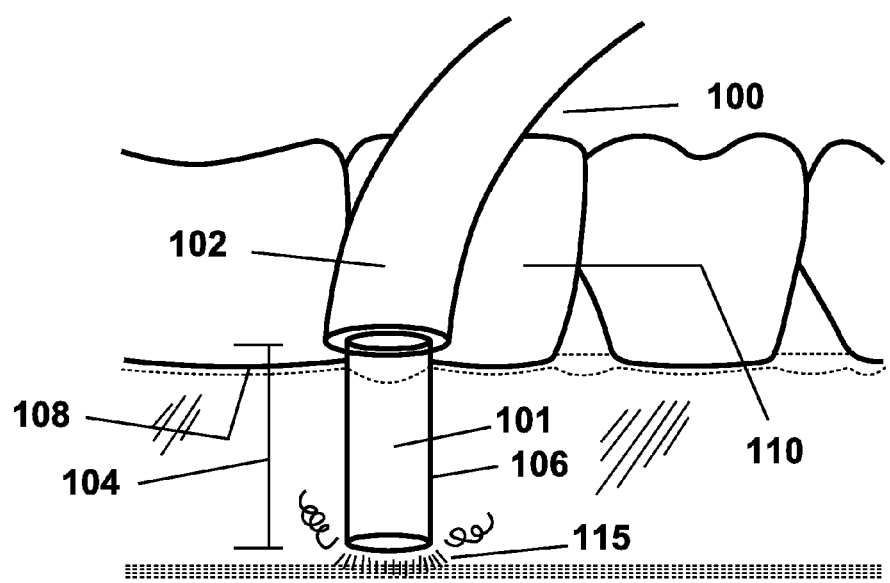
FIG. 6 illustrates a laser apparatus of the present invention being used to ablate infected tissue from the pocket region of a tooth exhibiting periodontitis.

In a yet further embodiment of the present invention—referred to herein as laser curettage—the following steps are performed leading to successful treatment of early-stage periodontal disease. First, the pocket depths are established using a periodontal probe. The pockets are then flooded throughout the entire pocket arch using the irrigation solution above described. Excess solution is then removed using a typical dental suction apparatus. The pockets are then irradiated with an 810 nm diode laser apparatus having a power output set from between about 1.0 to about 5.0 Watts or, more preferably, from between about 2.0 to about 4.0 Watts. Referring now to FIG. 6, in one embodiment, the laser apparatus 100 includes a fiber optic cable 101 surrounded by a cladding layer 102. A length 104 of the cladding layer 102 about 1-2 mm greater than the measured pocket depth is then stripped and cleaved from the fiber of the laser apparatus 100 to form a bare fiber optic portion 106. The stripped and cleaved portion 106 of the fiber 101 is then inserted into the periodontal pocket, where the bare fiber optic portion 106 lightly contacts the sulcus lining just inside the crest of the gingiva 108 while resting against a tooth 110. Using very light pressure, the lasing commences using short paint brush-like strokes around the circumference of the tooth with the laser energy being directed at infected or inflamed tissue 115 with sufficient intensity to ablate the infected or inflamed tissue.

This process will create a small trough between the tooth and gingiva. The suction apparatus or sterile cotton gauze or the like is then used to remove or extricate tissue from the treatment area or tissue that attaches to the fiber. The treatment is repeated over the entire arch. Upon completion, the pockets of entire arch are again flooded with the irrigation solution. The treatment may be repeated on a monthly basis until recovery is complete. In a yet further embodiment, patients with advanced periodontal disease are treated with an interim sulcular disinfection treatment, one embodiment of which is described below, which is performed intermittently between periodic treatments using the laser curettage routine.

Figure 7:
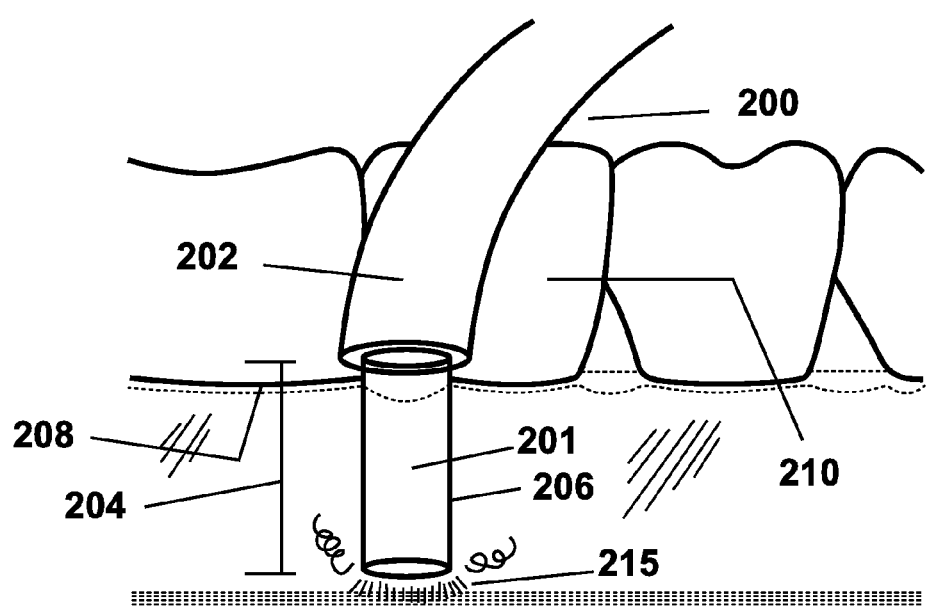
FIG. 7 illustrates a laser apparatus of the present invention being used to destroy pathogens from the pocket region of a tooth exhibiting periodontitis using the sulcular disinfection technique.

In an even further embodiment of the present invention—referred to herein as sulcular disinfection—the following steps are performed leading to successful treatment of early-stage periodontal disease. In a further embodiment, the same or similar steps may be performed intermittently with or following treatment by laser curettage. First, the pocket depths are established using a periodontal probe. The pockets are then flooded throughout the entire pocket arch using the irrigation solution above described. The pockets are then irradiated with an 810 nm laser apparatus having a power output set from between about 0.1 to about 0.5 Watts or, more preferably, from between about 0.2 to about 0.4 Watts. Referring now to FIG. 7, in one embodiment, the laser apparatus 200 includes a fiber optic cable 201 surrounded by a cladding layer 202. A length 204 of the cladding layer 202 approximately equal to the measured pocket depth is then stripped and cleaved from the fiber optic cable 201 of the laser apparatus 200 to form a bare fiber optic portion 206. The stripped and cleaved portion of the fiber is then inserted into the periodontal pocket, where the bare fiber optic portion 206 lightly contacts the sulcus lining just inside the crest of the gingiva 208 while resting against the tooth 210. Using very light pressure, the lasing commences using short paint brush-like strokes around the circumference of the tooth, with the laser energy being directed at infected or inflamed tissue 215 with sufficient intensity to destroy pathogens. Each tooth should receive an average of 15 seconds of laser treatment time. Problematic areas may be lased for longer treatment times. Areas of increased infection may be lased for 20-25 seconds per tooth. The treatment just described is repeated over the entire arch. Upon completion, the pockets over the entire arch are flooded again with the irrigation solution. The treatment is preferably repeated on a bi-monthly to monthly regimen. If the patient overall shows little to no periodontal improvement within 3-4 scheduled treatments then the following additional embodiment of treatment should be performed.

Although the present invention has been described with reference to preferred embodiments, numerous modifications and variations can be made and still the result will come within the scope of the invention. No limitation with respect to the specific embodiments disclosed herein is intended or should be inferred.

What is claimed is:

1. A method of treating periodontal disease comprising:
   measuring a pocket depth in a periodontal pocket;
   pre-flushing the periodontal pocket with a fluid containing an antimicrobial agent;
   obtaining an apparatus capable of generating radiant energy, the apparatus having a fiber optic cable surrounded by a cladding layer;
   removing a length of cladding layer from an end of the fiber optic cable approximately equal to the pocket depth creating a bare fiber optic portion;
   inserting the bare fiber optic portion into the periodontal pocket;
   directly applying radiant energy to an area of infected tissue in a periodontal pocket exhibiting periodontitis sufficient to ablate the infected tissue; and
   post-flushing the periodontal pocket with the fluid containing an antimicrobial agent.

2. The method of claim 1 further comprising the step of directing the radiant energy to the infected areas with a flexible fiber optic guide.

3. The method of claim 2, further comprising the step of generating the radiant energy from a source selected from the set of sources consisting of: a gas laser, a solid state laser, a diode laser, and an 810 nm diode laser.

4. The method of claim 1, further comprising the step of generating the radiant energy from a source selected from the set of sources consisting of: a gas laser, a solid state laser, a diode laser, and an 810 nm diode laser.

5. The method of claim 1, wherein the antimicrobial agent is selected from the set of antimicrobial agents consisting of: chlorhexidine gluconate, chlorhexidine, hydrogen peroxide, sodium hypochlorite, and sodium chlorite.

6. The method of claim 1, further comprising the step of applying sulcular disinfection.

7. The method of claim 6, wherein the method of sulcular disinfection comprises the following steps:
   directly applying a second radiant energy to an area of infected tissue in a periodontal pocket exhibiting periodontitis sufficient to destroy pathogens; and
   flushing the periodontal pocket with a fluid containing an antimicrobial agent.

8. The method of claim 6 further comprising the step of directing the second radiant energy to the infected areas with a second flexible fiber optic guide.

9. The method of claim 8, further comprising the step of generating the second radiant energy from a source selected from the set of sources consisting of: a gas laser, a solid state laser, a diode laser, and an 810 nm diode laser.

10. The method of claim 6, wherein both the steps of directing the radiant energy and the second radiant energy to the infected area are performed using the same radiant source.

11. The method of claim 6, wherein the step of applying sulcular disinfection comprises applying sulcular disinfection at least twice monthly.

12. The method of claim 6, wherein the method of sulcular disinfection is applied over the entire arch area of a tooth.

* * * * *